United States Patent [19]
Jamroz et al.

[11] Patent Number: 5,270,546
[45] Date of Patent: Dec. 14, 1993

[54] METHOD AND APPARATUS FOR NON-CONTACT, RAPID AND CONTINUOUS MOISTURE MEASUREMENTS

[75] Inventors: Wes R. Jamroz, Montreal; Julien Tremblay, Dollard des Ormeaux; Brian Wong, Montreal, all of Canada

[73] Assignee: MPB Technologies Inc., Dorval, Canada

[21] Appl. No.: 875,482

[22] Filed: Apr. 29, 1992

[51] Int. Cl.⁵ .................. G01N 21/00; G01N 21/17; G01N 21/47

[52] U.S. Cl. .................. 250/341; 250/340; 250/358.1; 250/359.1

[58] Field of Search .......... 250/340, 341, 358.1, 250/359.1, 360.1; 356/445, 447, 446

[56] References Cited

U.S. PATENT DOCUMENTS

| | | | |
|---|---|---|---|
| 3,748,473 | 7/1973 | Chen | 250/392 |
| 3,851,175 | 11/1974 | Dahlin et al. | 250/339 |
| 3,965,356 | 6/1976 | Howarth | 250/343 |
| 4,052,615 | 10/1977 | Cho | 250/341 |
| 4,266,878 | 5/1981 | Auer | 356/419 |
| 4,300,049 | 11/1981 | Sturm | 250/339 |
| 4,465,929 | 8/1984 | Edgar | 250/252.1 |
| 4,577,104 | 3/1986 | Sturm | 250/339 |
| 4,612,802 | 9/1986 | Clarke et al. | 73/73 |
| 4,632,561 | 12/1986 | Rosencwaig et al. | 356/446 X |
| 4,634,856 | 1/1987 | Kirkham | 250/557 X |
| 4,652,757 | 3/1987 | Carver | 250/341 X |
| 4,733,078 | 3/1988 | Sturm | 250/339 |
| 4,755,678 | 7/1988 | Izatt et al. | 250/358.1 |
| 4,766,319 | 8/1988 | Regimand | 250/390 |
| 4,788,853 | 12/1988 | Bell | 73/73 |
| 4,823,008 | 4/1989 | Sturm | 250/339 |
| 4,840,706 | 6/1989 | Campbell | 250/339 X |
| 4,879,471 | 11/1989 | Dahlquist | 250/359.1 |
| 4,928,013 | 5/1990 | Howarth et al. | 250/339 |

FOREIGN PATENT DOCUMENTS

| | | | |
|---|---|---|---|
| 1189192 | 6/1985 | Canada. | |
| 61-4945 | 1/1986 | Japan | 250/341 |
| 1259164 | 9/1986 | U.S.S.R. | 250/341 |

Primary Examiner—Constantine Hannaher
Assistant Examiner—Edward J. Glick
Attorney, Agent, or Firm—Wegner, Cantor, Mueller & Player

[57] ABSTRACT

A method and apparatus for non-contact determination of the moisture content in moving or stationary mass of fibrous products such as wood is provided. The method comprises irradiation of a substance with infra-red radiation which is intense enough to introduce microstructural modifications of the substance surface. The moisture content of the substance is determined by analyzing density of these surface modifications. It has been found, that an optical beam may be used in order to quantify the density of the surface modifications. The surface is scanned with the optical beam two (2) times. The first scanning is done prior to the infra-red irradiation; the second scanning is done following the infra-red irradiation. The invented method allows for non-contact, rapid and continuous in-line measurements of the moisture content.

25 Claims, 5 Drawing Sheets

METHOD AND APPARATUS FOR NON-CONTACT, RAPID AND CONTINUOUS MOISTURE MEASUREMENTS

FIELD AND BACKGROUND OF THE INVENTION

This invention concerns a new method and apparatus for in-line measurements of moisture contents in wood pieces, logs, lumber, veneer and the like. The common method of moisture measurements is based on determining of the difference in the weight of the substance before and after heating it at the temperature above the boiling point of water (usually at 105° C.). However, such method requires long periods of time (24 hours or longer). That method is limited mostly to stationary measurements and it is not practical for in-line applications where virtually instantaneous water content measurements are required.

Another method of moisture determination is based on spectral selective optical absorption which can be measured in scattered and (or) transmitted beams. Sets of light sources with precisely selected wavelengths are used in that method. One set of the wavelength(s) is utilized as a reference which is relatively unaffected by the characteristic (e.g. moisture content) being measured. The other set of the wavelength(s) is tuned to the water absorption peak. Several versions of this approach have been disclosed, in which either conventional infra-red optical sources (e.g. U.S. Pat. Nos. 4,266,878, 4,634,856, 4,788,853, 3,851,175, 3,965,356, 4,052,615, 4,300,049, 4,465,929, 4,577,104, 4,733,078, 4,823,008, 4,840,706, 4,879,471, 4,928,013) or a submillimeter laser (U.S. Pat. No. 4,755,678) were applied. These methods were disclosed for moisture measurements either in soil or in paper products.

Moisture measurements based on absorption of fast neutron rays and gamma radiation were disclosed in U.S. Pat. Nos. 4,766,319 and 3,748,473.

Electrical meters based on measurements of an electrical property of a substance are used for the moisture content measurements where a relationship between the electrical property and the moisture content of a substance can be established. The moisture content of a substance may be estimated from electrical properties such as resistance, capacitance and conductivity. However, these type of meters are limited to lower end of the moisture content [according to The Standard Test Methods (ASTM: D 4444-84) the moisture content range for the electrical meters is from 6% to 27%]. The electrical meters can not be used efficiently outside that range of the moisture content because higher moisture levels cause no substantial change in electrical properties.

A method of non-contact moisture measurements is disclosed in U.S. Pat. No. 4,612,802 issued Sep. 23, 1986 to Forintek Canada Corporation. In that method, an area of one surface of a substance is subjected to a predetermined intensity of a heat source for a selected period of time. The moisture content is determined from measurements of the temperature rise of the heated surface of the substance.

SUMMARY OF INVENTION

In accordance with this invention, a method and apparatus for non-contact and rapid measurements of the moisture content of a substance have been devised. The method and apparatus are derived from the fact that infra-red radiation is absorbed by water which is present in a substance. The surplus of this infra-red radiation causes modifications of a substance surface by changing its microstructure. It has been experimentally demonstrated, that a relationship exists between the moisture content of a substance and the density of surface modifications caused by intense infra-red radiation. Simply, it has been found that a substance with a lower water content will be affected stronger by the intense infra-red radiation than a substance with higher water content exposed to the same amount of the infra-red radiation. Furthermore, it has been determined, that the density of surface modifications can be translated into a quantitative measure by using an optical beam. An optical beam is scanned along an analyzed portion of a substance surface. The surface is scanned two (2) times: prior to—and after—the surface modifications. The difference in intensities of scattered optical radiation is recorded by optical detector(s). It has been experimentally determined, that the moisture content is inversely proportional to a normalized intensity of the scattered optical radiation. Furthermore, it has been determined, that an analysis of a portion of a substance surface is sufficient for acceptably accurate approximation of the average moisture content of a substance.

It has been found, that the relationship between the moisture content and intensity of scattered optical radiation can be approximated by the following equation:

$$(I_{in} - I_f)/I_{in} = A - BM_c \qquad [1]$$

where:

$M_c$-is the moisture content;

$I_{in}$-is the intensity of scattered optical radiation from the analyzed portion of a substance surface prior to irradiation with infra-red radiation;

$I_f$-is the intensity of scattered optical radiation from the analyzed portion of a substance surface after it was irradiated with infra-red radiation;

A and B-are calibration constants.

The constants A and B are determined experimentally for a given substance. The values of $I_f$ and $I_{in}$ are measured by the optical detector(s).

The equation [1] is the 1-st order approximation of the relationship. This approximation may be extended by including higher order components in order to improve precision of the measurements.

The invented method allows for non-contact measurements of the average moisture content of a stationary as well as a fast moving substance. The main advantage of the method is that it provides means for the measurements over the entire range of the moisture content. The additional advantage of the method is that the apparatus can be placed at a distance from the analyzed substance because all the measurements may be carried out by low-divergence beams.

BRIEF DESCRIPTION OF THE DRAWINGS

The accompanying

FIG. 1 illustrates a schematic view of apparatus capable of measuring the moisture content in a stationary sample of a substance. The apparatus includes a single source of infra-red radiation, a single source of optical radiation, and an optical detector.

FIG. 2 illustrates a schematic view of apparatus capable of measuring the moisture content in a moving sample of a substance. The apparatus includes a single source of infra-red radiation, two sources of optical radiation, and two optical detectors.

FIG. 3 presents a graph plotting the percentage moisture content versus the normalized intensity of the scattered optical beam for spruce lumber.

FIG. 4 presents a graph plotting the percentage moisture content versus the normalized intensity of the scattered optical beam for balsam lumber.

FIG. 5 presents a graph plotting the percentage moisture content versus the normalized intensity of the scattered optical beam for pine lumber.

DESCRIPTION OF PREFERRED EMBODIMENTS

Figure 1:
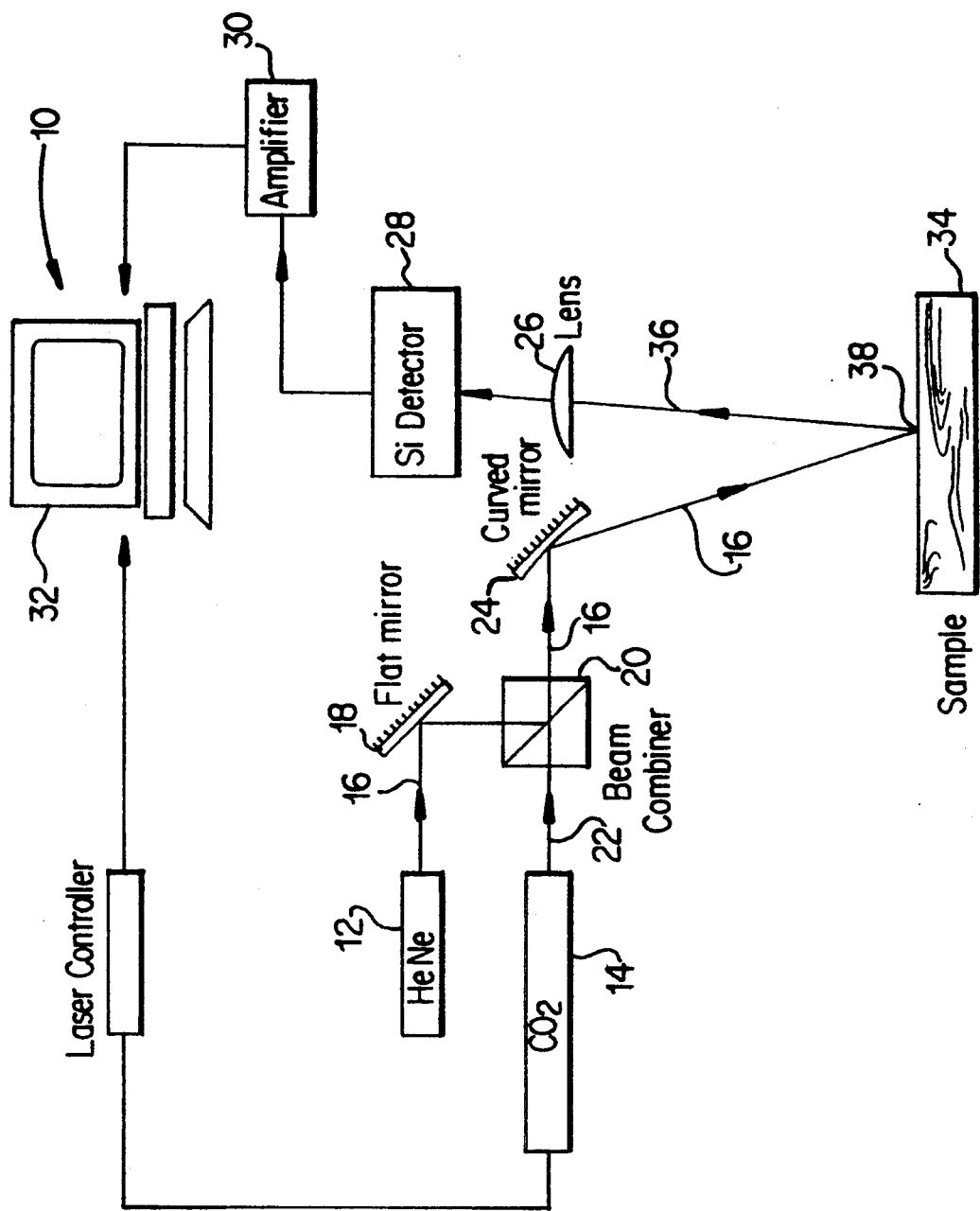
FIGS. 1 and 2 illustrate schematic views of two versions of the apparatus.

The apparatus embodiment illustrated in FIG. 1 is suitable for moisture measurements in a stationary sample of a substance. Referring to FIG. 1, the apparatus, generally designated by reference numeral 10, comprises an optical light source 12 such as a HeNe laser and a low-divergence light beam source 14 providing intense infra-red radiation. The optical light emitted from optical light source 12 is represented by arrow 16. Flat mirror 18 directs optical light 16 to beam combiner 20. The intense infra-red radiation emitted by low-divergence light beam source 14 is represented by arrow 22. Curved mirror 24 reflects both optical light 16 and intense infra-red radiation 18 after their passage through beam combiner 20. Lens 26 is provided to converge reflected light 36 to optical detector 28. Amplifier 30 amplifies the signal provided from detector 28. The components of the system are controlled by computer 32 which is equipped with a data acquisition board which is used for data recording and analysis. The arrangement of the optical axis of the detector and the radiation sources is such that they converge at the sample surface.

When it is desired to measure the moisture level of stationary sample 34, a selected area 38 of sample 34 is first scanned with optical beam 16 from HeNe laser 12 which has been reflected through mirrors 18 and 24 and passed through beam combiner 20. The reflected optical radiation, which is identified by arrow 36, is collected by lens 26, forwarded to optical detector 28 through amplifier 30 and recorded by computer 32. Selected area 38 of sample 34 is then irradiated by intense infra-red radiation 22 from low-divergence light beam source 14. The intense infra-red radiation 22 is combined to optical light 16 through beam combiner 20, preferably a ZnSe beam combiner. The intense infra-red radiation 22 is focused on selected area 38 of sample 34 through mirror 24. This scanning causes the microstructure of sample 34 to be modified at selected area 38. Following irradiation, selected surface 38 of sample 34 is scanned again with optical light 16 and the reflected intensity 36 is recorded by the optical detector 28. The average moisture content of selected area 38 is approximated by comparing the measured intensities of the reflected optical radiation before and after irradiation with the calibrated data for a given substance.

Figure 2:
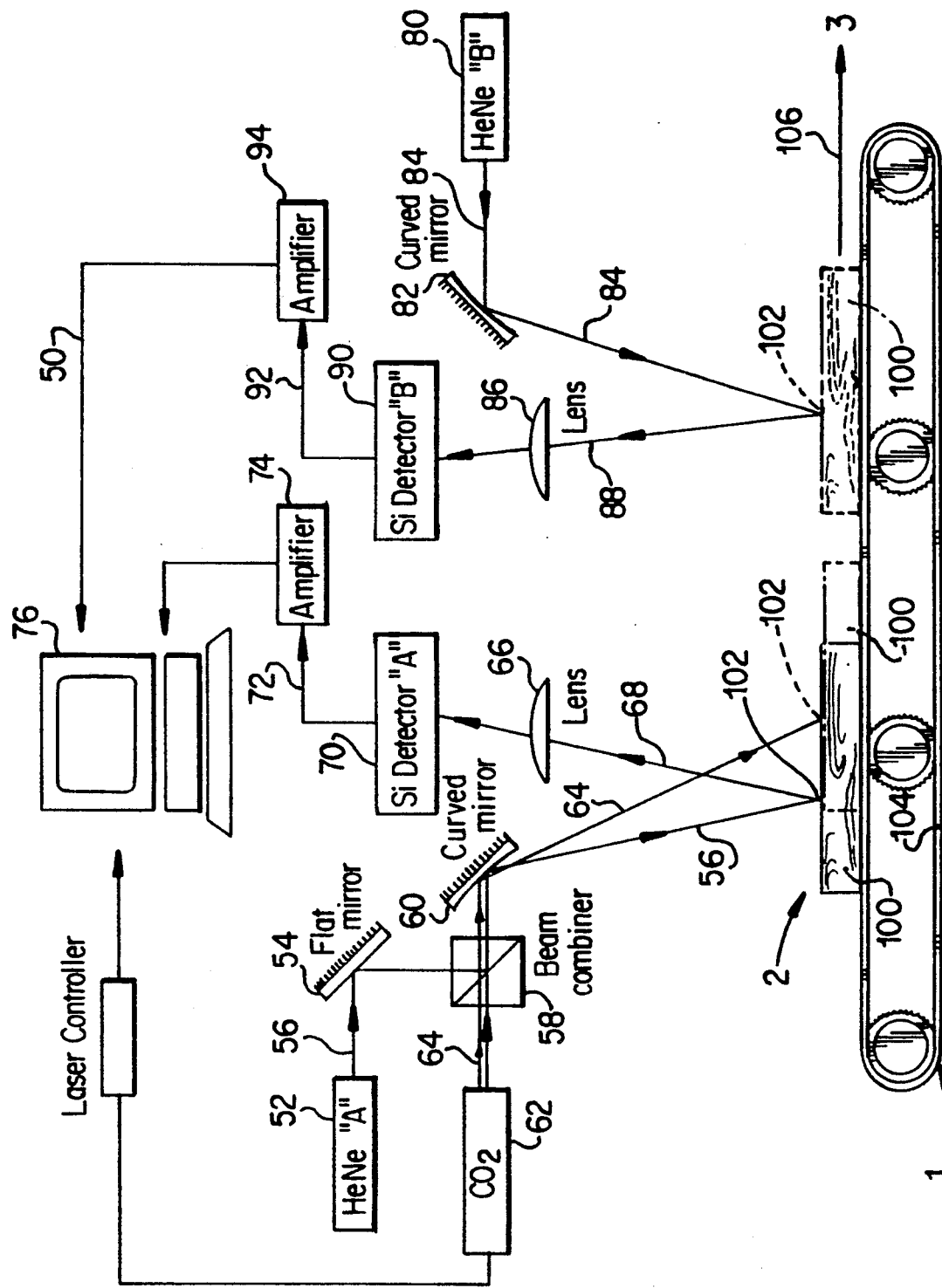

The apparatus embodiment illustrated in FIG. 2 is used in situations where moisture measurements are taken on moving samples. Referring to FIG. 2, the apparatus, generally designated by reference numeral 50, presents some similarities with the apparatus described in FIG. 1. Hence, the apparatus 50 comprises a first optical light source 52, a flat mirror 54 to reflect optical light 56 to beam combiner 58 and a curved mirror 60 to focus optical light beam 56. Also included is a low-divergence light beam source 62 which provides intense infra-red radiation 64. Lens 66 provides reflected optical light 68 to detector 70. The detected signal 72 is amplified through amplifier 74 and analyzed by computer 76.

The system 50 illustrated in FIG. 2 also comprises a further optical light source 80 which is also preferably a HeNe laser, a second curved mirror 82 to focus optical light 84 and a second lens 86 to provide reflected optical light 88 to detector 90. The detected signal 92 is amplified by amplifier 94 and analyzed by computer 76.

When it is desired to measure the moisture content of sample 100, at selected area 102, sample 100 is moved on conveyor 104 and selected area 102 is subjected to optical light 56. Reflected optical light 68 is analyzed through detector 70. The sample 100 which continuously moves on conveyor 104 is then irradiated at the same selected area 102 by intense infra-red radiation 64 which causes a modification of the microstructure of sample 100 at selected area 102. Sample 100 then continues its path in the direction of arrow 106 and is scanned again at selected area 102 by optical beam 84 from further light source 80. Reflected optical light 88 is then analyzed through second detector 90. The arrangement of the optical axis of the radiation sources and detectors is such that they are in line with respect to the direction 106 in which sample 100 is being moved. Detector 70 records the intensity of reflected optical radiation 68 prior to its irradiation with infra-red beam 64. The optical radiation reflected from the modified surface is then recorded by detector 90. The average moisture content of sample 100 is then approximated by comparing the measured intensities of the reflected optical radiation with the calibration data for a given substance.

In the following examples a $CO_2$ laser has been used as the source of infra-red radiation (MPB's model IN-70: wavelenght 10.6 micron, 60 Watt output power, 7 mm beam diameter, pulsed at 50 msec). HeNe lasers have been used as the sources of the optical beams (Melles Griot's model 05LHP 991: wavelength 0.6328 micron, 10 mWatt output power, 0.7 mm beam diameter). The curved mirror (1 meter radius of curvature, 1 inch diameter) was used to focus the laser beam on the samples. The distance between the sample surface and the mirror was approximately 0.5 meter. The optical detectors used were manufactured by EG&G (Model 30809). The computer was equipped with a data acquisition board (a 12 bit analog-to-digital converter).

It has been determined, that there is a linear relationship between the optimum intensity of the $CO_2$ laser beam and the speed of the conveyor. For example, the 60 Watt output power corresponds to the optimum speed of the conveyor of 120 feet per minute.

EXAMPLE I

Figure 3:
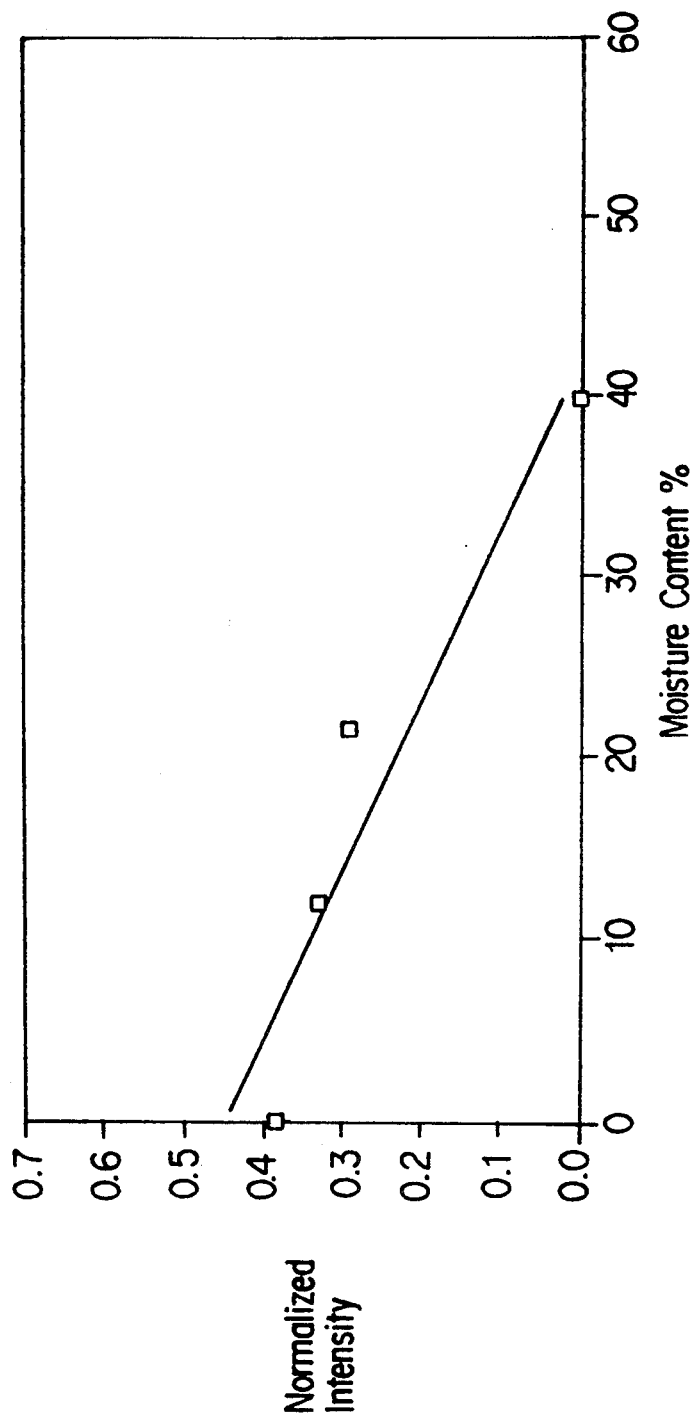
FIGS. 3, 4, and 5 illustrate data obtained by using exemplary apparatus for measuring the moisture content in accordance with this invention. Each point on FIGS. 3, 4 and 5 represents the mean value of 50 experimental measurements.

Pieces of two by four spruce lumber of different moisture contents were analyszed with the described apparatus. The samples were moving with the speed of 15 feet/minute. A $CO_2$ laser was used as the source of the infra-red radiation. The normalized intensity of the scattered HeNe laser radiation versus the average moisture content of the samples are plotted on FIG. 3. A close relationship between the intensity of the scattered optical radiation and the average moisture content is self evident. It is apparent, that the average moisture content can be determined with reasonable accuracy from the measurements of the normalized intensities of the scattered optical radiation.

EXAMPLE II

Figure 4:
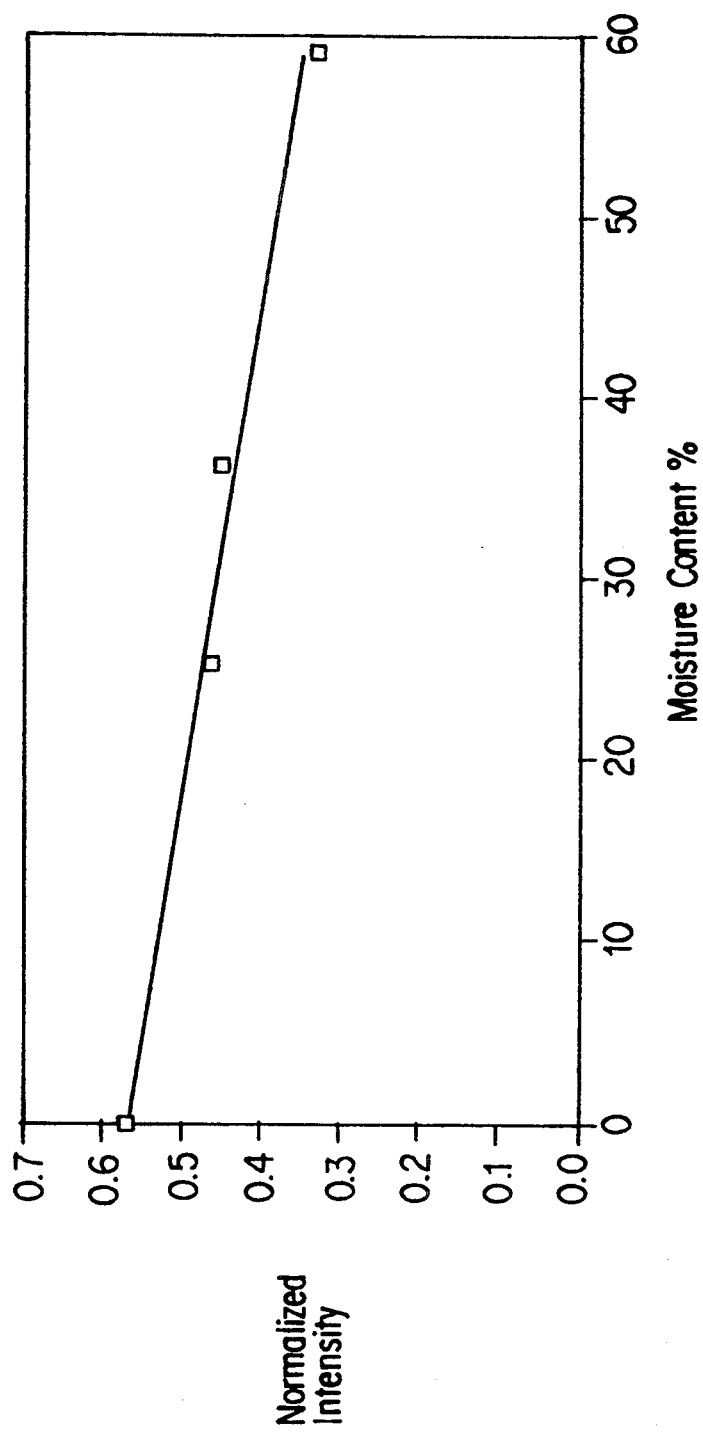

In this example, pieces of two by four pine lumber of different moisture contents were analyszed with the described apparatus. The samples were moving with the speed of 15 feet/minute. A $CO_2$ laser was used as the source of the infra-red radiation. The normalized intensity of the scattered HeNe laser beam versus the average moisture content are plotted on FIG. 4.

EXAMPLE III

Figure 5:
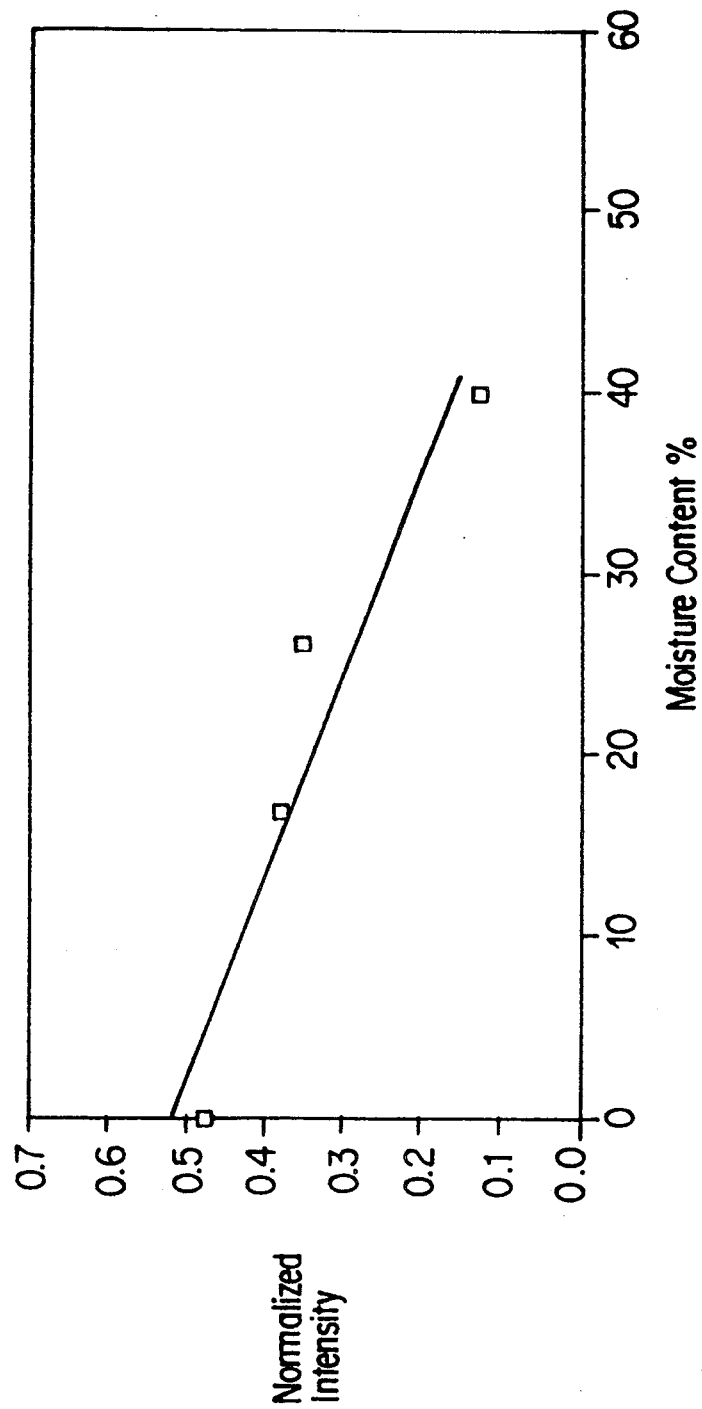

In this example, pieces of two by four balsam lumber of different moisture contents were analyzed with the described apparatus. The sample was moving with the speed of 15 feet/minute. A $CO_2$ laser was used as the source of the infra-red radiation. The normalized intensity of the scattered HeNe laser beam versus the average moisture content are plotted on FIG. 5.

We claim:

1. A method for the non-contact determination of the moisture content of a sample, said method comprising:
    subjecting said sample to an optical light beam of predetermined energy density and measuring the intensity of said optical light reflected from said sample;
    irradiating an area of said sample with a low-divergence light beam having a density level sufficient to produce modifications of the microstructure of said sample;
    subjecting said irradiated area to an optical light beam of known intensity and measuring the intensity of said optical light reflected from said irradiated area; and
    determining the moisture level of said sample by comparing the light reflected from said irradiated area to the light reflected from said sample prior to irradiation.

2. A method according to claim 1, wherein said low-divergence light beam source is a laser beam source.

3. A method according to claim 2, wherein said laser beam source is a $CO_2$ laser.

4. The method as claimed in claim 1, wherein said sample is moving.

5. A method for the non-contact determination of the moisture content of a sample, said method comprising:
    subjecting said sample to a first optical light beam of predetermined energy density and measuring the intensity of said first optical light reflected from said sample;
    irradiating an area of said sample with infra-red light having a density level sufficient to produce modifications of the microstructure of said sample;
    subjecting said irradiated area to a second optical light beam of predetermined energy density and measuring the intensity of said second optical light reflected from said sample; and
    determining the moisture level of said sample by comparing said first and second optical light reflections to predetermined sample optical reflection data.

6. The method as claimed in claim 5, wherein said sample is moving.

7. An apparatus for measuring the moisture content of a wood product, said apparatus comprising in combination:
    a light source for subjecting a selected area of said wood product to optical light;
    a low-divergence light beam source for irradiating said selected area of said wood product at an energy density sufficient to modify the microstructure of said wood product at said selected area; and
    a detector positioned relative to said light source to measure the intensity of light reflected by said selected area of said wood product when illuminated by said light source before and after said selected area has been irradiated with said low-divergence light beam source.

8. An apparatus according to claim 7, further comprising amplifier means for amplifying the signal resulting from the measure of the intensity of reflected light measured by said detector.

9. An apparatus according to claim 8, further comprising means to calculate the moisture level of said wood product by comparing the intensity of light reflected by said selected area of said wood product before and after irradiation of said selected area with said low-divergence beam source.

10. An apparatus according to claim 7, wherein said low-divergence light beam source is a laser beam source.

11. An apparatus according to claim 10, wherein said laser beam source is a $CO_2$ laser.

12. An apparatus for measuring the moisture content of a wood product, said apparatus comprising in combination:
    a first light source for subjecting a selected area of said wood product to an optical light beam of known intensity;
    a low-divergence light beam source for irradiating said selected area of said wood product at an energy density sufficient to modify the microstructure of said wood product at said selected area;
    a further light source for subjecting said wood product to an optical light beam of known intensity at said selected area after said selected area has been irradiated by said low-divergence light beam source; and
    detector means positioned relative to said first and further light sources to measure the intensity of light reflected by said wood product when illuminated by said first and further light sources.

13. An apparatus according to claim 12, wherein said detector means comprise:
    a first detector associated with said first light source to measure the intensity of light reflected by said selected area when illuminated by said first light source before said selected area has been irradiated with said low-divergence light beam source; and
    a second detector associated with said further light source to measure the intensity of light reflected by said selected area when illuminated by said further light source after the selected area has been irradiated with said low-divergence light beam source.

14. An apparatus according to claim 13, wherein said first and second detectors are coupled with amplifier means for amplifying the signal resulting from the measure of the intensity of reflected light measured by said first and second detectors.

15. An apparatus according to claim 14, further comprising means to calculate the moisture level of said wood product by comparing the intensity of light reflected by said selected area of said wood product before and after irradiation of said selected area with said low-divergence beam source.

16. An apparatus according to claim 12, wherein said low-divergence light beam source is a laser beam source.

17. An apparatus according to claim 16, wherien said laser beam source is a $CO_2$ laser.

18. A method for the non-contact determination of the moisture content of a wood product, said method comprising:

subjecting said wood product to a first optical light beam of known intensity and measuring the intensity of said first optical light reflected from said wood product;

irradiating an area of said wood product with a low-divergence light beam having a density level sufficient to produce modifications of the microstructure of said wood product;

subjecting said irradiated area to a further optical light beam of known intensity and measuring the intensity of said second optical light reflected from said wood product; and determining the moisture level of said wood product by comparing said first and further optical light reflections to predetermined wood product optical reflection data.

19. The method as claimed in claim 18, wherein said wood product is moving.

20. A method according to claim 18, wherein said low-divergence light beam source is a laser beam source.

21. A method according to claim 19, wherein said laser beam source is a $CO_2$ laser.

22. A method of determining relative variations in the approximate average moisture content of a wood piece regardless of the thickness of said wood piece at different locations therealong, comprising:

(a) subjecting each one of a plurality of preselected areas on any surface of said wood piece to optical radiation of known intensity and measuring the initial intensity of said optical radiation reflected from said preselected areas on said surface of said wood piece;

(b) subjecting said preselected areas on said surface of said wood piece to modifications of their microstructure by irradiating said selected areas with infra-red radiant energy of predetermined energy density to yield structurally modified preselected areas;

(c) subjecting said structurally modified preselected areas to optical radiation of known intensity and measuring the intensity of optical radiation reflected from said structurally modified preselected areas; and (d) comparing the intensity of optical radiation reflected from said structurally modified preselected areas of said wood piece with said initial intensity of optical radiation reflected from said preselected areas on the surface of said wood piece to determine the average moisture content of said wood piece.

23. A method according to claim 22, wherein said wood piece is moving.

24. A method according to claim 22, wherein said low-divergence light beam source is a laser beam source.

25. A method according to claim 24, wherein said laser beam source is a $CO_2$ laser.

* * * * *